(12) United States Patent
Yonezawa et al.

(10) Patent No.: US 8,692,023 B2
(45) Date of Patent: Apr. 8, 2014

(54) SUGAR METABOLISM IMPROVING COMPOSITION, AND PHARMACEUTICAL PREPARATION CONTAINING SAID COMPOSITION

(71) Applicant: Erina Co., Inc., Tokyo (JP)

(72) Inventors: Takayuki Yonezawa, Tokyo (JP); Je-Tae Woo, Tokyo (JP); Kazumi Yagasaki, Tokyo (JP)

(73) Assignee: Erina Co., Inc., Tokyo (JP)

( * ) Notice: Subject to any disclaimer, the term of this patent is extended or adjusted under 35 U.S.C. 154(b) by 0 days.

(21) Appl. No.: 13/744,893

(22) Filed: Jan. 18, 2013

(65) Prior Publication Data

US 2013/0245325 A1  Sep. 19, 2013

Related U.S. Application Data

(63) Continuation of application No. PCT/JP2011/056931, filed on Mar. 23, 2011.

(30) Foreign Application Priority Data

Jul. 30, 2010 (JP) .................................. 2010-171687

(51) Int. Cl.
*C07C 49/83* (2006.01)
*A61K 31/121* (2006.01)
*A61K 36/70* (2006.01)

(52) U.S. Cl.
USPC .......................................... 568/328; 514/682

(58) Field of Classification Search
USPC ........................................... 568/328; 514/682
See application file for complete search history.

(56) References Cited

U.S. PATENT DOCUMENTS

| 2004/0126367 A1 | 7/2004 | Fujii |
| 2006/0177888 A1 | 8/2006 | Cynshi |

FOREIGN PATENT DOCUMENTS

| CN | 101224242 | * | 7/2008 |
| JP | S61-66787 | | 4/1986 |
| JP | 2000-103742 | | 4/2000 |
| JP | 2003-26625 A1 | | 1/2003 |
| JP | 2005-325025 A1 | | 11/2005 |
| JP | 2008-273978 A1 | | 11/2008 |
| KR | 10-2006-0078125 A | | 7/2006 |
| WO | WO 2004/083869 A1 | | 9/2004 |

OTHER PUBLICATIONS

Mei et al. New seco-anthraquinone glucosides from Rumex nepalensis. Planta Medica, 2009, vol. 75 (10), pp. 1162-1164; HCAPLUS Document No. 153:638017 (abstract).*
Batterham et al. Coloring matters of Australian plants. VIII. Naphthalene derivatives from Dianella. Austalian Journal of Chemistry, 1961, vol. 14, pp. 637-42. HCAPLUS Document No. 58:3157 (abstract).*
Drug Information; Glimiran Tablets; http://www.info.pmda.go.jp/go/pack/3961007F1190_1_04/3961007F1190_1_04?view=body, (2012).
International Search Report for International Application No. PCT/JP2011/056931 dated Apr. 19, 2011.
English translation of the international preliminary report on patentability (Chapter II of the PCT) mailed Feb. 14, 2013.

* cited by examiner

*Primary Examiner* — Sikarl Witherspoon
(74) *Attorney, Agent, or Firm* — Kratz, Quintos & Hanson, LLP

(57) ABSTRACT

The purpose of the present invention is to provide a highly safe composition that improves glucose tolerance and sugar metabolism at skeletal muscles, and a prevention/treatment drug for diabetes/metabolic syndrome containing the composition. Provided is a composition that is for improving sugar metabolism and glucose tolerance and that contains a compound represented by formula (I) derived from a plant selected from the group consisting of *Rumex japonicus*, *R. crispus*, and *R. obtusifolius* as the active ingredient.

8 Claims, 6 Drawing Sheets

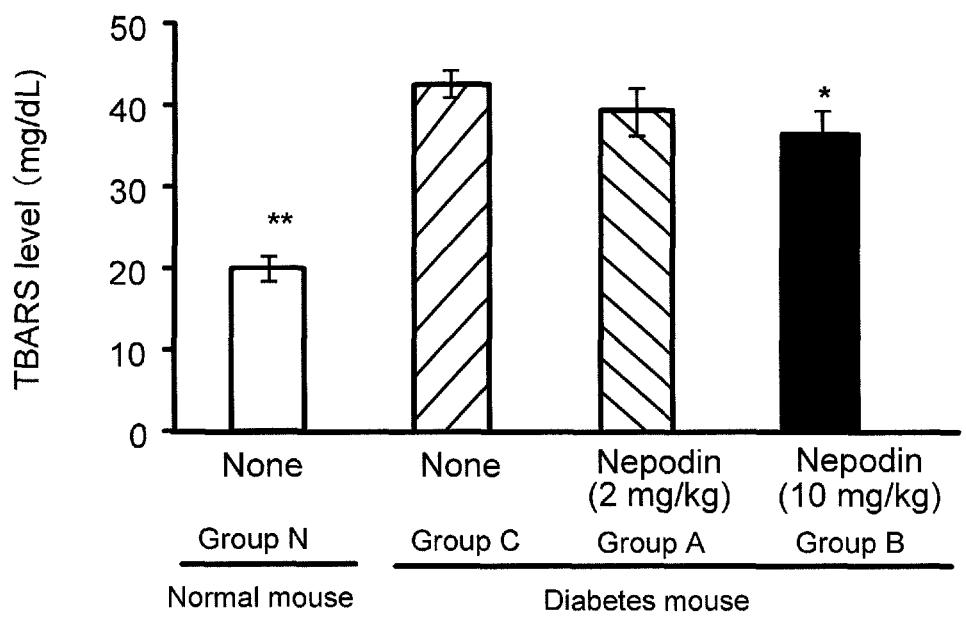

SUGAR METABOLISM IMPROVING COMPOSITION, AND PHARMACEUTICAL PREPARATION CONTAINING SAID COMPOSITION

A composition for ameliorating glucose metabolism and lipid metabolism, and a pharmaceutical preparation comprising thereof.

TECHNICAL FIELD

The present invention relates to a composition for ameliorating glucose metabolism and lipid metabolism, and a pharmaceutical preparation comprising thereof for prophylaxis or treatment of metabolic syndrome.

BACKGROUND ART

Recently, patient number of adult disease such as diabetes and so forth, which is caused by changing of diet or life style, is increasing, and some means are needed. Here, the adult disease is defined as a concept including many diseases such as diabetes derived from life style, hypertension, hyperlipidemia, pneumonectasia caused by smoking, or the like. Among the adult disease, metabolic disease is defined that visceral fat accumulation type obesity, of which visceral fat area is not less than 100 cm$^2$, and it complicated two indexes among following three: triglyceride level is not lower than 150 mg/dL, or LDL cholesterol level is less than 40 mg/dL), upper level of blood pressure (systolic blood pressure is not lower than 130 mmHg, or diastolic blood pressure is not lower than 85 mmHg), and hyperglycemia (fasting blood sugar is 110 mg/dL). The metabolic syndrome is a comorbid disease more than two of the above three indexes.

It is known that, in relationship between diet and the adult disease, high fat diet induced obesity that causes systemic insulin resistant to develop diabetes, hyperlipidemia, and hypertension. Furthermore, it is also recently clarified that these become risk factors to cause arteriosclerotic cardiovascular disease. Therefore, prophylaxis of insulin resistant and treatment thereof are important.

Here, insulin resistant is defined that "the decrease of insulin action in skeletal muscle, liver, and, adipose tissues as target tissues thereof". The type 2 diabetes recently becoming popular is defined that "the disease caused by decrease of insulin secretion from n-cells in pancreas, and decrease of insulin action in skeletal muscle, liver, and adipose tissues as target tissues thereof".

Conventionally, as a treating agents for diabetes, sulfonylurea agents (SU urea agent) such as tolbutamide, gliclazide, glimepiride, and so forth, a fast-acting Insulin secretion booster such as nateglinide, mitiglinide calcium compound and so forth, phenylalanine derivative agents, biguanide drugs such as metformin, buformin and so forth, insulin-sensitizing agent such as pioglitazone, rosiglitazone, and so forth, thiazolidines have been developed and used (see, non-patent document, hereinafter, it is referred to as the "prior art 1").

Other than such western medicine, the patent publication, JP2000-103742 A, discloses that ethanol extract from several plants including nagaba gishigishi (*Rumex crispus*), of which root is subjected to be extracted, shows amylase inhibition activities in vitro (see, patent document No. 1, hereinafter, it is referred to as the "prior art 2"). Also, the other patent publication, JP2005-325025 A, discloses that water extracts from 24 kind of crude medicine (crude drug) including kogane gishigishi (*R. maritimus*), which is belonging to the same species as *Nagaba Gishigishi*, have blood sugar level decreasing effect for rat with alloxan-induced diabetes (see, patent document 2, hereinafter, it is referred to as the "prior art 3").

PRIOR ART

Patent Document

[Patent document 1] JP 2000-103742
[Patent document 2] JP 2005-325025

Non-Patent Document

[Non-patent document 1] Pharmaceutical preparation interview form Glimilan tablet, Gliclazide, revised in July, 2010 (Version 4) Standard product class number in Japan 873961

SUMMARY OF THE INVENTION

Problem to be Solved by the Invention

SU urea agent described on the prior art 1 is excellent that it is the insulin secretion promoter (inulin secretagogue), and may be administered per os. However, since it sometimes causes thick and delayed type hypoglycemia, there is the problem that it should be carefully administered to the patients having disorders in sympathetic nerve function, having disturbance of consciousness, aged people who cannot recognize that hypoglycemia, the patient who cannot respond to hypoglycemia. Also, it makes the patient body weight gain.

Since biguanide agents promote the metabolism of pyruvic acid into lactic acid in the liver of the patient, it sometimes cause the problem that the patients have lactic acid acidosis when it is administrated to aged patients, those with decreased liver functions or kidney and cardiac functions, those take a lot of alcohols.

On the other hand, pioglitazone, PPARγ agonist, does not have side effects such as weight gain and the like; it shows excellent effect to improve the insulin resistance. However, it show the side effect such as weight gain or fat volume, when it is administrated for long time.

The prior art 2 relates to the inhibition of α-amylase activity which decompose polysaccharide such as starch and the like into disaccharide such as maltose and the like, or monosaccharide such as glucose and the like. At present, α-amylase inhibitor is not used as the antidiabetic, glucose inhibitor (αGI agent), a sugar analog, is used. α-glucosidase inhibitor (α-glucosidase inhibitor) is an excellent agent that decreases the blood glucose level after meals, and inhibits the postprandial hyperglycemia by taking it with the mal.

However, it is not effective for other treatment of hyperglycemia except decreasing the postprandial hyperglycemia. Also, it has side effects such as flatulence, feeling of fullness, abdominal discomfort, diarrhea, and the like. Further, there is the problem that it causes hepatic damage by constitution.

On the other hand, the improvement of insulin resistance or the treatment of diabetes is classified into a diet therapy, ergotherapy, and medical therapy. Among them, it is known that the ergotherapy remarkably improves the insulin resistance.

When the diabetes develops, the blood sugar level and the like are controlled by combined therapy of them. If the blood sugar level is well controlled, the symptom is not deteriorated. Therefore, the diabetes patient may continue the almost same life as that of healthy people. This means that the treatment for the improvement of insulin resistance and the diabetes takes long term. Therefore, there are strong needs for the pharmaceutical preparations that satisfy the conditions that the preparation has lesser effects for viscera functions such as a liver, a kidney and the like, and which are less likely to secondarily non-react even when it is administrated for long time, because they are needed.

Since skeletal muscle is the largest tissue for receiving sugar from blood, decrease of sugar uptake in the muscle causes development of systemic insulin resistance. Therefore, it is desired for the agent to be used for the prophylaxis or the treatment of insulin resistance or diabetes that they have improvement activity of sugar metabolism in the skeletal muscle.

Some components contained in plants used as a crude drug, which have been used for long time. Therefore, there are merits that less side effect has already confirmed, when compounds fulfill the above-mentioned requirements are screened.

On the other hand, there are many diabetes patients more than 16,000,000 including reserves for the diabetes development. Therefore, there is the problem whether it is sufficient amount of agent for the diabetes patients is supplied Means for Solving the Problem The inventors of the present invention are eagerly studied under the above-mentioned environment. They chose the crude drug to be provided in sufficient amount, and then searched a variety of compounds included in them, salt thereof, hydrate thereof to be used for improving glucose metabolism.

As a result, they found new function of nepodin (nepodin; 2-Acetyl-1,18-dihydroxy-3-methylnaphthalene; dianellidin (dianellidin); musizin (musizin or musizine)), which abound in gishigishi (of which another the like and used as the crude drug having laxative property, that has regulation function for glucose metabolism in the muscle cell. Then, they completed the present invention.

Namely, the first aspect of the present invention is a 5'-adenocine monophosphate-activated protein kinase activating agent comprising at least one substance selected from the group consisting of a compound shown in the following chemical formula (I), a pharmacologically acceptable salt thereof, and a pharmacologically acceptable hydrate thereof as an active ingredient.

[Chemical formula 1]

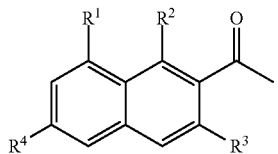

(I)

In the formula, $R^1$ to $R^4$ independently show one of a substitute selected from the group consisting of a hydrogen atom, hydroxyl group, alkyl group having a carbon number 1 to 3, alkoxy group having the carbon number 1 to 3, and acyl group having the carbon number 1 to 3, respectively. $R^1$ and $R^2$ are a functional group independently selected from the group consisting of hydroxyl group, methoxy group, ethoxy group, and acetyl group respectively, $R^3$ and $R^4$ are a functional group independently selected from the group consisting of a hydrogen atom, methyl group, and ethyl group, respectively.

Here, the compound shown in the above-mentioned formula (I) is preferably that shown in the following formula (II) (nepodin: 2-Acetyl-1,8-dihydroxy-3-methyl-napthalene).

[Chemical formula 2]

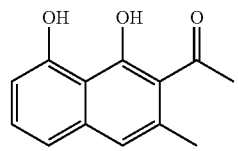

(II)

The second aspect of the present invention is a glucose uptake accelerating agent into a muscle comprising an AMPK activating agent, which is comprising at least one compound shown in the above-mentioned formulae (I) or (II) as the active ingredient. Here, $R^1$ to $R^4$ are the same as those of above.

Further, the third aspect of the present invention is a glucose tolerance improving agent comprising the AMPK activating agent, which is comprising at least one compound shown in the above-mentioned formulae (I) or (II) as the active ingredient. Here, the $R^1$ to $R^4$ are the same as those of above. The fourth aspect of the present invention is a blood lipid level reducing agent comprising the AMPK activating agent, which is comprising at least one compound shown in the above-mentioned formulae (I) or (II) as the active ingredient. Here, the $R^1$ to $R^4$ are the same as those of above.

The fifth aspect of the present invention is prevention and/or treatment agent for metabolic syndrome above-mentioned formulae (I) or (II) as the active ingredient. Here, the $R^1$ to $R^4$ are the same as those of above.

[Chemical formula 3]

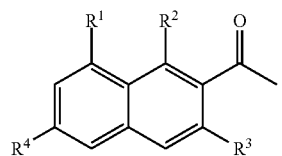

(III)

In the formula, $R^1$ to $R^4$ independently show one of substitute selected from the group consisting of a hydrogen atom, hydroxyl group, alkyl group having a carbon number 1 to 3, alkoxy group having a carbon number 1 to 3, and acyl group having a carbon number 1 to 3, respectively. $R^1$ and $R^2$ are a functional group independently selected from the group consisting of hydroxyl group, methoxy group, ethoxy group, and acetyl group respectively; $R^3$ and $R^4$ are a functional group independently selected from the group consisting of a hydrogen atom, methyl group, and ethyl group, respectively.

Here, the composition for ameliorating glucose metabolism and lipid metabolism preferably comprises at least one of the substance selected from the group consisting of the compound shown in the above-mentioned formula (III), that shown in the following formula (IV), pharmacologically acceptable salts thereof, and pharmacologically acceptable hydrate thereof as an active ingredient.

[Chemical formula 4]

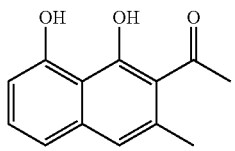

(IV)

The compound, a pharmacologically acceptable salt thereof, and pharmacologically acceptable hydrate thereof, which are included in the composition, is preferably derived from at least a plant selected from the group consisting of Gishigishi (*Rumex japonicas*), Nagaba Gishigishi (*R. crispus*) and ezono gishigishi (*R. obtusifolius*).

The sixth aspect of the present invention is the pharmaceutical composition for ameliorating glucose metabolism and lipid metabolism for recovering glucose tolerance comprising at least one substance selected from the group consisting of a compound shown in the above-mentioned formula (III) or (IV), pharmacologically acceptable salts thereof, and pharmacologically acceptable hydrate thereof as an active ingredient.

The seventh aspect of the present invention is the prophylaxis and/or treatment agent for improving glucose tolerance comprising the composition for ameliorating glucose metabolism and lipid metabolism. The eighth aspect of the present invention is the prophylaxis and/or treatment agent for metabolic syndrome comprising the composition for ameliorating glucose metabolism and lipid metabolism.

Advantageous Effect of the Invention

According to the AMPK activating agent of the present invention, it may activate AMPK in the muscle cells. According to the glucose uptake accelerating agent of the present invention, it comprises the AMPK activating agent as the active ingredient. By this, it may suppress the increase of the blood glucose level by accelerating the glucose uptake into the muscle cell, when the human or animal takes the composition. Also, it may decrease the blood glucose level which was once increased by improving the glucose tolerance, when the human or animal takes the composition.

Also, according to the glucose tolerance improving agent may improve the insulin resistance, because it comprises the AMPK activating agent as the active ingredient. Therefore, has the advantageous effects for the prevention and/or the treatment of the diabetes, as well as recovering or improving glucose tolerance.

Also, the blood lipid level reducing agent of the present invention may decrease the level of the neutral lipid such as neutral fat, cholesterol, and the like.

Further, the prophylaxis and/or treatment agent for metabolic syndrome comprises the AMPK activating agent as the active ingredients. Therefore, it has functions such as accelerating the glucose into the muscle cells, suppressing the increase of the blood glucose, decreasing the blood glucose level, improving the glucose tolerance, and reducing the blood lipid level.

BRIEF DESCRIPTION OF THE DRAWINGS

FIG. 8C is the graph showing TBARS values of the normal and diabetes mice.

MODE FOR CARRYING OUT THE INVENTION

Figure 1:
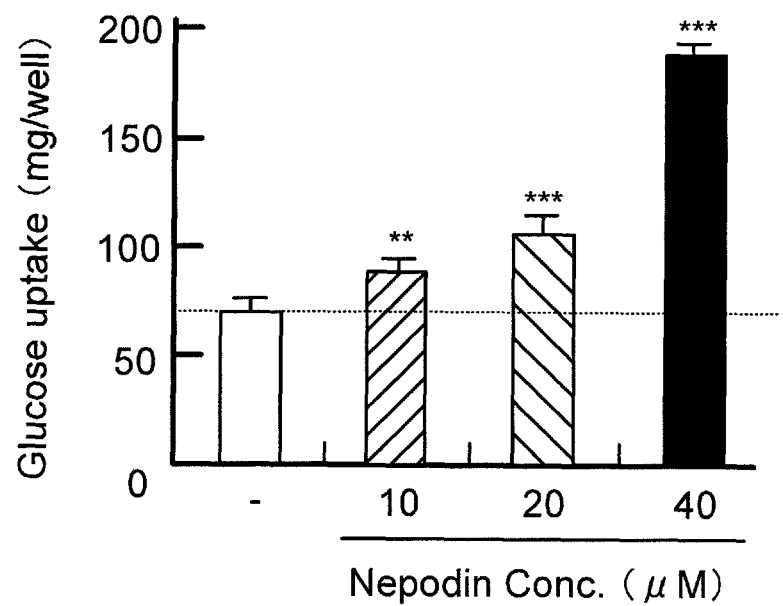
FIG. 1 is a graph to show the effect of nepodin for the glucose uptake into L6 myotube cells.

Hereinbelow, we explain the present invention in detail.

The first aspect of the present invention is a composition for ameliorating glucose metabolism and lipid metabolism comprising at least one substance selected from the group consisting of a compound shown in the following chemical formula (I), a pharmacologically acceptable salt thereof, which are derived from at least one of a plant selected from the group consisting of, gishigishi (*Rumex japonicas*), nagaba gishigishi (*R. crispus*), and ezono gishigishi (*R. obtusifolius*), and a pharmacologically acceptable hydrates thereof as an active ingredient.

[Chemical formula 5]

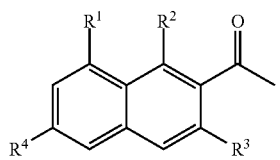

(I)

In the formula, $R^1$ to $R^4$ independently show one of substitute selected from the group consisting of a hydrogen atom, hydroxide group, alkyl group having a carbon number 1 to 3, an alkoxy group having the carbon number 1 to 3, and an acyl group having the carbon number 1 to 3, respectively. Among them, it is preferable that $R^1$ to $R^4$ are independently selected from the group consisting of the hydroxyl group, the methoxy group, ethoxy group, and acetyl group, because it has the effect to accelerate the glucose uptake into the muscle cells. Also, in the formula (I), $R^1$ and $R^2$ are independently selected from the group consisting of the hydroxyl group, methoxy group, ethoxy group, and the acetyl group; $R^3$ and $R^4$ are a functional group independently selected from the group consisting of the hydrogen atom, methyl group, and ethyl group, and the acetyl group.

Concretely, it is preferable that the composition comprises at least one substance selected from the group consisting of the compound shown in the following formula (II), pharmaceutically acceptable salt thereof, and pharmaceutically acceptable hydrate hereof.

[Chemical formula 6]

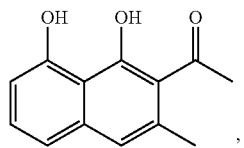

(II)

Another aspect of the present invention is the composition for ameliorating glucose metabolism and lipid metabolism for glucose tolerance comprising at least one substance selected from the group consisting of a compound shown in the following chemical formula (III), pharmacologically acceptable salts thereof, and pharmacologically acceptable hydrates thereof, which is selected from the group consisting of gishigishi (*Rumex japonicas*), nagaba gishigishi (*R. crispus*) and ezono gishigishi (*R. obtusifolius*), as an active ingredient. Wherein, the composition for ameliorating glucose metabolism and lipid metabolism for glucose tolerance ameliorates the glucose metabolism and lipid metabolism, and it ameliorates the glucose tolerance as a part of this.

[Chemical formula 7]

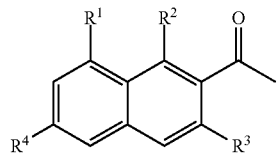

(III)

Wherein, in the formula, $R^1$ to $R^4$ are the same as those of the formula (I).

The present invention is also the composition for ameliorating glucose metabolism and lipid metabolism for glucose tolerance comprising at least one substance selected from the group consisting of a compound shown in the following chemical formula (IV), pharmacologically acceptable salt thereof, and pharmacologically acceptable hydrate thereof as an active ingredient.

[Chemical formula 8]

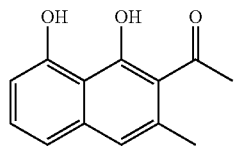

(IV)

Wherein, gishigishi (*Rumex japonicas*) is a weed spread out on the whole land of Japan and it is usually shown around a road side, crest of paddy, and others. It extends the stem, of which length is about 1 m, and it bears clustered flowers similar to those of buckwheat, *Fagopyrum esculentum*. Nagaba gishigishi (*R. crispus*, originally from Europe) or ezono gishigishi (*R. obtusifolius*) are belonging to the same congenic species of Gishigishi, and they may be used instead of Yotei.

Roots of Gishigishi have been used under the name of Yotei as the crude drug. In Japanese Kampo, it has pharmaceutical effects such as loosening the bowel, diuretic effect, and homeostasis effect, and is used for constipation, bladder inflammation, hemorrhoidal bleeding, skin disorder and the like. In folk remedy, its roots are grated to be mixed with a small portion of vinegar, and they are applied to dermatomycosis such as ring worm infection, *tinea alba* infection, athlete's foot and the like. Nagaba gishigishi has a laxative action similar to Rehm belonging to Polygonaceae.

It is known that the roots of Gishigishi include chrysophanol, emodin, chrysophanol anthrone, nepodin, oxalic acid and the like, and they have antibacterial effect, anticoagulant action, and the like.

There are mentioned as closely related plant to Gishigishi, karafuto-daiou (*Rumex gmelini*), kibunedaiou (*Rumex nepalensis*), scientific name (*Rumex hastatus*), scientific name (*Rumex alpinus*), sorrel (*Rumex acetosa*), scientific name (*Rumex cripus*), scientific name (*Rumex stenophyllus*), scientific name (*Rumex patientia*), scientific name (*Rumex chalepensis*), and scientific name (*Rumex orientalis*).

As closely related plants to Polygonaceae, there are mentioned, for example, *dianella* (*Dianella ensifolia*) belonging to *Dianella* in Liliaceae, scientific name (*Dianella revolute*) or scientific name (*Dianella callicarpa* (Liliaceae)) or scientific name (*Dianella nigra*) in Liliaceae, *Hemerocallis flava* var. *minor* (*Hemerocallis minor*) *Hemerocallis* in Liliacwae, scientific name (*Simethis* bicolor Kunth) in Agavaceae, scientific name (*Limonium myrianthum*) belonging to *Limonium* in Plumbaginaceae, scientific name (*Rhamnus prinoides*) in Rhamnaceae, scientific name (*Rhamnus wightii*), scientific name (*Rhamnus procumbens*), and scientific name (*Maesopsis eminii*), and scientific name (*Myrsine africana*) colicwood in Myrsinaceae.

The compounds shown in the above-mentioned formulae (I) to (IV) and analogs thereof are synthesized by the known method or according to it, or are purchased as commercially available ones to be used. Also, they may be obtained from the above-mentioned plant sources by using extraction or isolation.

Among the plant sources, it is preferable to use roots of gishigishi, karafutonodaiou, kibunedaiou, nagaba gishigishi, ezono gishigishi, *Rumex hastatus, Dianella ensifolia, Dianella callicarpa* (Liliaceae), *Dianella nigra, Hemerocallis flava* var. minor or *Myrsine africana*, leaves of *Rhamnus prinoides*, or bark of *Rhamnus wightii*.

Hereinbelow, one example for isolating nepodin and the analog thereof from Gishigishi is shown.

The roots of Gishigishi, which are dug up around the season withering scape (from July to September) and their rootlets are removed, are fully dried in the sun. Dried Gishigishi is broken; then a predetermined amount of it is weighed, and ethanol is added to extract its contents. Subsequently, obtained concentrated extract solution is firstly subjected to partitioned extraction by using water and organic solvent. Then, the obtained organic phase is again subjected to the partitioned extraction by using high-polar solvent except water and low polar solvent. The obtained liquid phases are respectively subjected to the partitioned chromatography to obtain fractions, which are studied their activities of glucose incorporation by myotube cells as an index. Among the fractions those having high activities are collected to be concentrated, and then they are used to partially purified products.

For example, 1 to 4 L of ethanol is poured to about 100 to 400 g of the roots of Gishigishi (dried) to obtain an extract by performing ethanol extraction for 1 to 10 days in room temperature. The obtained extract is filtrated, and then the solvent is evaporated by using, for example, a rotary evaporator, flash evaporator and the like. Then, the concentrate is subjected to the partitioned extraction by using, for example, water: ethyl acetate (0.1:1 to 2:1). After that, the ethyl acetate phase obtained is subjected to the partitioned extraction again by using methanol with water (aqueous methanol) and n-hexane again. When the aqueous methanol is used, it is preferable to use the methanol of which water content is 5 to 20% (v/v), because of its extraction efficiency.

Subsequently, the obtained methanol phase is concentrated, and then the concentrate is subjected to a preparative chromatography by using ODS as the solid phase, water—methanol as a mobile phase, for example, Cosmosil $75C_{18}$-OPEN (NACALAI TESQUE, INC.) as the solid phase and water–methanol=20-80 to 40-60 as the mobile phase.

Each fraction may be concentrated to obtain the extracts including the above-mentioned compounds or nepodin.

As described above, the compounds shown in the above-mentioned chemical formulae and analogs thereof are obtained from the extracts from Gishigishi. Nagaba Gishigishi or ezono gishigishi, belonging to the same genus as gishigishi, is used; the compounds and the analogs thereof may be obtained as described above.

The compounds and the analogs thereof obtained are subjected to Mass Spectrometry (MS), nuclear magnetic resonance analysis (NMR) and the like to obtain spectrum data. Then, the data is compared to those on reference data to decide their structures.

Evaluations of the glucose metabolism improvement by the extracts are performed to measure incorporated amount of glucose in incubated muscle cells, when the muscle cells, for example, rat myoblast cell, L6, are incubated in the medium including glucose to which the extracts are added in a predetermined amount for the predetermined period.

Concretely, the incorporated amount of glucose is determined by incubating the cell for proliferating into the myotube cell, a model of the muscle cell, at 37° C. for 5 to 15 days in the medium, for example, Dulbecco's MEM (it is referred to as "DMEM" hereinbelow) supplemented with predetermined antibiotics. Subsequently, the medium is changed to the Krebs-Henseleit buffer including 5 to 15 µM of glucose supplemented with 5 µM to 50 µM of nepodin for the predetermined period, and the cells are incubated in the buffer.

Also, the evaluation of glucose tolerance improvement is performed by time-dependently measuring the change of blood glucose level, between the fasting blood glucose level when the predetermined amount of nepodin is administrated to a diabetes model animal or a metabolic syndrome model animal (hereinafter, they are referred to as the "diabetes model animal" or the "diabetes model mouse"), and that after the glycemic load.

In particular, nepodin is administrated to the diabetes model animal at the amount of 1 to 20 mg/kg body weight for several weeks. After short time fasting, for example, fasting of 2 to 18 hr, blood is drawn to measure the blood glucose level. By this, the effect for fasting blood glucose level may be evaluated. Also, the predetermined period, long time fasting, for example 12 to 20 hr fasting, is performed, and then glucose is administrated p. o. or i. p. Then, the blood is drawn in time-dependently. By this, the effect for glucose tolerance may be evaluated.

Furthermore, the improvement of lipid metabolism is evaluated by determining the amounts of neutral fat (triglyceride) and that of cholesterol in sera or organs of the diabetes model animal. In particular, 1 to 20 mg/kg body weight of nepodin is administrated to the diabetes model animal for several weeks. The animal is sacrificed upon termination, and then the blood is drawn and the organs are excised to determine the amounts of neutral fat (triglyceride) and cholesterol in the organs, the amounts of neutral fat (triglyceride) and total cholesterol. By this, the lipid metabolism may be evaluated.

It is known that thiobarbituric acid reactive substance (hereinafter, it is sometimes referred to as "TBARS") such as malondialdehyde (MDA: malondialdehyde) and the like is generated by peroxidation of lipid. The increased TBARS causes diabetes of metabolic syndrome exacerbation factor. Therefore, the effects for prevention and/or treatment diabetes or metabolic syndrome are evaluated by using the evaluation of the decreasing effect of TBARS.

The compounds shown in the formulae (I) to (IV), the physiologically or pharmaceutically acceptable salts thereof, and the hydrates thereof can be used to formulate the pharmaceutical preparation described in below.

When nepodin is used solely to form the pharmaceutical preparation, the crystalline as described above is treated in accordance with the conventional method. Then, they may be mixed with an excipient and the like as described later to produce any pharmaceutical preparation selected from the group consisting that for improving glucose and lipid metabolism, that for improving glucose and lipid metabolism to improve the glucose tolerance (hereinafter, it is sometimes referred to as "glucose tolerance improving agent"), that for prophylaxis or treatment of diabetes, and that for prophylaxis or treatment of metabolic syndrome.

As the pharmaceutical preparation comprising the pharmaceutical composition as an active ingredient, there are mentioned such as, for example, parenteral agent such as injections, suppositories, aerosols, transdermal system, and the like; non-parenteral agent such as tablets, powders, capsules, pills, troches, liquids and solutions, and the like. In the specification, the tablets include sugar-coated tablets, coat tablets, and buccal tablets, and the capsules includes both of hard capsules and soft capsules. Also, the granules include coated granules. The liquids and solutions include suspensions, emulsions, syrups, elixirs, and the syrups include fry syrups.

Note that the above-mentioned preparations include both of non-sustained ones and sustained ones.

These preparations may be formulated according to the known procedure by using pharmacologically acceptable carrier, excipient, disintegrator, lubricant, colorant, and so forth, for formulating the preparation, described on Japanese Pharmacopoeia.

As these carriers or excipients, for example, there are mentioned such as lactose, glucose, sucrose, mannitol, potato starch, corn starch, calcium carbonate, calcium phosphate, calcium sulfate, crystalline cellulose, powdered glycyrrhiza extract, powdered gentian, and so forth.

As a binder, for example, there are mentioned such as the starch, tragacanth gum, gelatin, syrup, polyvinyl alcohol, polyvinylether, polyvinylpyrrolidone, hydroxypropylcellulose, methylcellulose, ethylcellulose, carboxymethylcellulose, and so forth.

As the disintegrator, for example, there are mentioned such as starch, agar, powdered gelatin, sodium carboxymethylcellulose, calcium carboxymethylcellulose, crystalline cellulose, calcium carbonate, sodium bicarbonate, sodium alginate and so forth; as the lubricant, for example, there are mentioned such as magnesium stearate, talc, hydrogenated vegetable oil, macrogol and so forth.

The colorant, which is acceptable to be added to the pharmaceutical preparation, can be used with no limitation. Except these additives, a corrigent and so forth can be used depending on the necessity.

When formulating the tablet or the granule, if necessary, they may be coated by using sucrose, gelatin, hydroxypropylcellulose, purified shellac, gelatin, glycerin, sorbitol, ethylcellulose, hydroxy-propyl-cellulose, hydroxypropylmethylcellulose, polyvinylpyrrolidone, acetate cellulose phthalate, hydroxypropylmethylcellulose phthalate, methyl-methacrylate, methacrylate polymer, and so forth to have single coating or plural coatings.

Furthermore, the capsule can be prepared by encapsulating the granule or powdered preparation into the capsule made of ethylcellulose, gelatin, and so forth.

When the injectable is prepared by using the above-mentioned compound, the physiologically acceptable salt thereof, or the hydrate thereof, a PH regulator, a buffering agent, a stabilizer, a solubilizing agent, and so forth may be added as needed.

When one of the preparation for improving glucose and lipid metabolism, that for improving glucose and lipid metabolism to improve the glucose tolerance (hereinafter, it is sometimes referred to as "glucose tolerance improving agent"), that for prophylaxis or treatment of diabetes, and that for prophylaxis or treatment of metabolic syndrome is administrated to a patient, the dosage is depending on conditions such as thickness of the symptom, age, weight, and health status and so forth. In general, the preparation is administrated for an adult in the parenteral or non-parenteral route, at the dosage of 1 to 2,000 mg/kg, preferably 1 to 1,000 mg/kg once a day or more. Number of administration and amounts a day can be adjusted depending on the conditions described above optionally.

Example 1

(1) Reagents, Etc.

Nepodin, glucose, sodium pyruvate, magnesium sulfate, potassium dihydrogen phosphate, potassium chloride, sodium chloride, potassium chlorid.dihydrate, sodium bicarbonate and bovine serum albumin, streptomycin and penicillin G were purchased from Wako Pure Chemical Industries Ltd. Fetal bovine serum, D-MEM, and Hepes were purchased from SIGMA Co. Inc.

Rat myoblast strain L6 cells were purchased from ATCC (American Type Culture Collection).

(2) Study for Effects on Glucose Metabolism

L6 myoblast cells were suspended at concentration of $12.5 \times 10^4$ cells/mL in a D-MEM medium with 5.5 mM of glucose concentration to which 10% v/v fetal bovine serum, 100 µg/mL of streptomycin, and 100 U/mL of penicillin G were added.

The cells were inoculated at the concentration $5 \times 10^4$ cells/well (0.4 mL/well) in 24 well multi-plate (NUNC Co., Inc.); then cultured in a 5% $CO_2$ incubator at 37° C. for 11 days. The medium was exchanged every 3 days.

After 11 days, the culture medium was replaced with filter sterilized Krebs solution (Krebs-Henseleit buffer; pH 7.4, 141 mg/L of $MgSO_4$, 160 mL/L of $KH_2PO_4$, 350 mg/L of KCL, 6,900 mg/L of NaCl, 373 mg/L of $CaCl_2.2H_2O$, and 2,100 mg/L of $NaHCO_3$) (KHH buffer) supplemented with 0.1% bovine serum albumin, 10 mM of Hepes, and 2 mL of pyruvate sodium but without glucose to maintain the cells in the 5% $CO_2$ incubator at 37° C. for 2 hours.

Next, each KHH buffer was prepared: only 11 mM glucose was added, or 11 mM of glucose and nepodin (10 µM, 20 µM, or 40 µM). The medium was replaced to either one of them to culture the cells in the 5% $CO_2$ incubator at 37° C. for further 4 hours.

Glucose concentrations in the culture solution at the beginning and after 4 hours from the culture start were determined by using a microplate reader (Beckman Coulter, Inc. AD200) and a glucose determination kit (Glucose CII test Wako (Wako Pure Chemical Industries, Ltd.), Catalog number 439-90901). The decreased amount of glucose in the culture solution was obtained from the calculation of the difference between glucose concentrations in the culture medium before and after the culture, and it was set as a glucose intake by the cells.

Results are shown in FIG. 1. The glucose intake by L6 myotube cells were cultured in the medium without nepodin is 69.4±10.4 mg/well (average±SD, n=6).

In contrast, those of L6 myotube cells cultured in the medium with nepodin 10 to 40 µM were dose-dependently improved on the concentration of nepodin. Particularly, the glucose intake was largely improved to 188.3±4.4 mg/well when 40 µM of nepodin was added in the medium (n=6).

The above-mentioned experiments, both of proliferation and the glucose intake, were performed without insulin. According to the results, it was considered that the above glucose intake by rat myoblast strain, L6 cells, was derived from an insulin independent action.

Example 2

The effect of nepodin administration was decided by determining the amount of a phospholylated AMPK (5' adenosine monophosphate-activated protein kinase), which was important for glucose metabolism in L6 myotube cells, as an activation index.

(1) Methods

The same reagents as those of EXAMPLE 1 were used here.

L6 myoblast cells were suspended in D-MEM (5.5 mM of glucose concentration) supplemented with 10% v/v fetal bovine serum, 100 µg/mL of streptomycin, and 100 U/mL of penicillin G so as to become the cell concentration at $12.5 \times 10^4$ cells/well.

L6 myoblast cells were inoculated into a 6 cm diameter dish (FALCON Co., Inc.) (2 mL/well) so as to become the concentration at $5 \times 10^5$ cells/well, and cultured in the 5% $CO_2$ incubator at 37° C. for 11 days. The medium was exchanged every 3 days.

After 11 days from the culture start, the medium is replaced to Krebs solution (Krebs-Henseleit buffer; pH 7.4, $MgSO_4$ 141 mg/L, $KH_2PO_4$ 160 mL/L, KCL 350 mg/L, NaCl 6,900 mg/L, $CaCl_2.2H_2O$ 373 mg/L, and $NaHCO_3$ 2,100 mg/L) (it is referred to as "KHH buffer" hereinbelow) supplemented with 0.1% bovine serum albumin, 10 mM of Hepes, and 2 mL of sodium, pyruvate without glucose, which was filtered for sterilization. Then, the cells were cultured in the 5% $CO_2$ incubator at 37° C. for 2 hours.

Next, one KHH buffer supplemented with 11 mL of glucose only or another one supplemented with both 11 mL of glucose and nepodin (30 µM) was prepared. The medium was changed either one of the buffer the cells were further cultured in the 5% $CO_2$ incubator at 37° C. for each time.

After the termination of the culture, the cells were washed with PBS, the cells were lysed by adding cytolytic buffer (Tris-HCL (pH 7.4), 150 mM NaCl, 1% NP-40, 0.5% sodium deoxycholate, 0.1% sodium dodecyl sulfate (SDS), 0.5 mM dithiothreitol, 0.2 mg/mL Pefabloc SC (Pefabloc SC, Roche Diagnostics K. K.) with 1 mM of $Na_3VO_4$ (sodium vanadate, Wako Pure Chemical Industries, Ltd) into each well. The cytolytic buffer is collected from each well, and treated with sonication. Then, it was centrifuged at 12,000×g, for 15 minutes and supernatant was collected to be prepared as samples for western blotting.

The negative control samples were prepared by using the cytolytic buffer to be added to the cells cultured with the medium including DMSO, the solvent of nepodin, at the same amount as nepodin. The negative control sample and the samples were separated by using SDS-PAGE according to the conventional method, and were analyzed by using anti-phosphorylated AMPK antibody and anti-AMPK antibody by the western blotting.

(2) Results

Figure 2:
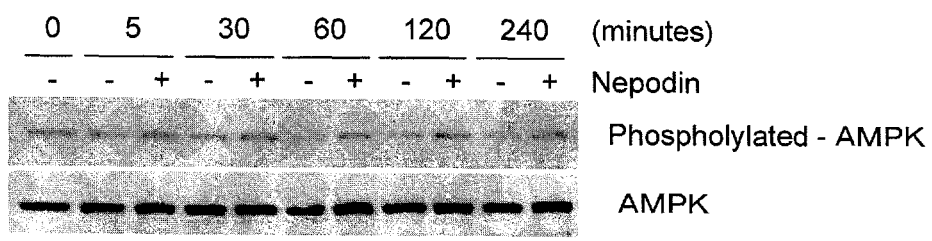
FIG. 2 is a stained image of protein electrophoresis showing time depending change of AMPK level and phosphorylated AMPK level, during culture of L6 myotube cells in a medium with nepodin.

Results are shown in FIG. 2. Phosphorylated AMPK in L6 myotube cells increased up to 120 minutes in the medium with nepodin. This means that nepodin activated AMPK in the myotube cells.

Example 3

Effect of nepodin was evaluated by using fasting blood glucose of model mice (db/db mouse) having diabetes II as an index.

(1) Methods

The reagents were used the same as those used in the Example 1 as long as there is no special note.

Nepodin was suspended in 0.5% carboxymethylcellulose aqueous solution (Wako Pure Chemical Industries, Ltd.). Male mice of 5 week old, BKS. Cg-+Lerp$^{db}$/+Lerp$^{db}$/J mouse (db/db diabetes model mouse, hereinafter, it is referred to as "diabetes model mouse") for a test group (nepodin administration group) were purchased from Charles River Laboratories Japan Inc. Prior to the test, they were maintained for 1 week under the condition of 12 h light/12 h dark at a room temperature approximately 25° C., feeding normal diet. It is considered that db/db mouse also becomes a model for a metabolic syndrome model, because it is obese and has higher levels of variety of lipid.

Heterozygous male mice of 5 week old, BKS. Cg-+Dock 7$^m$/+Lerp$^{db}$/J mouse (normal mouse) for a negative control group (without nepodin administration) were purchased from Charles River Japan Inc. Prior to the test, they were maintained as the same condition as those of the test group.

The test group mice were divided into 3 groups: C group (positive control group; n=10) with no nepodin administration; A group (n=6) to which nepodin was administered at the dose of 2 mg/kg/day or 10 mg/kg/day for 5 weeks; and B group (n=6). 0.5% carboxymethylcellulose aqueous solution without nepodin was administered to the negative control group (N group; n=6) and the positive control group (C group) under the same conditions as described above. Feeds and water are freely given to each group.

Blood samples were obtained from the tail vein of the mice after 4 hour fasting per week. The blood glucose level was measured by using Glucose CII test Wako (Wako Pure Chemical Industries, Ltd.)

(2) Results

In the diabetes model mice, there was no significant difference of average amount of feed intake and body weight gain between A group (nepodin administration group) and C group (no nepodin administration group), or B group (nepodin administration group) and C group (no nepodin administration group) (See Table 1).

TABLE 1

| | mouse | | | |
|---|---|---|---|---|
| | Normal mice | | Diabetes mice | |
| | Group Name | | | |
| | N | C | A | B |
| nepodin administration (mg/kg/day) | None | None | 2 | 10 |
| Feed intake (g/day) | 2.62 ± 0.29 | 5.35 ± 0.60 | 5.26 ± 0.61 | 5.40 ± 0.50 |
| Weight gain (g/5 weeks) | 4.17 ± 0.89 | 17.8 ± 2.04 | 18.7 ± 1.76 | 19.45 ± 2.68 |

Figure 3:
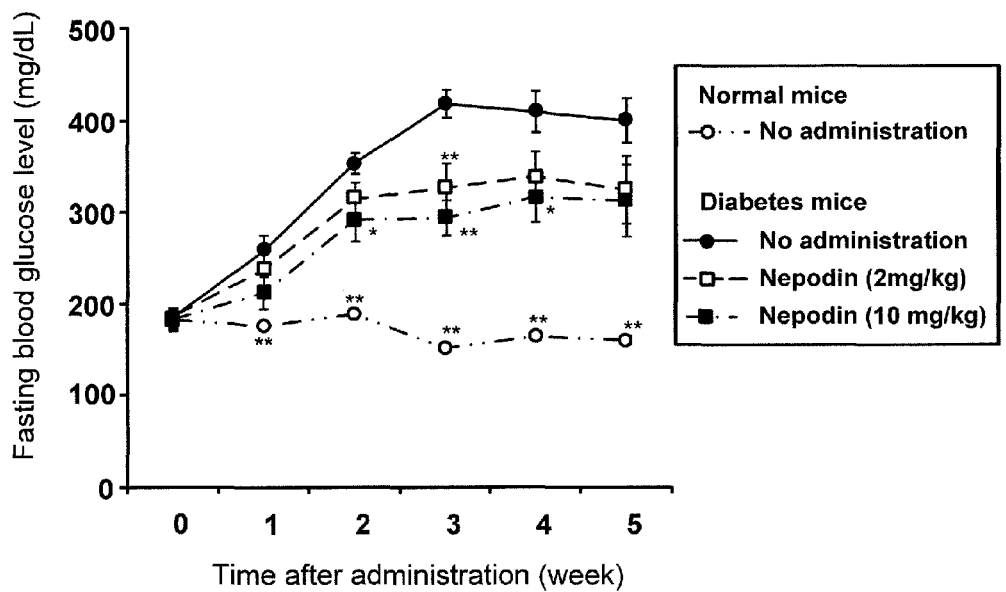
FIG. 3 is a graph showing the time dependent change of the fasting blood glucose level, when nepodin is given to the diabetes model mouse.

On the other hand, the fasting blood glucose level was significantly lower in the nepodin-administrated diabetes model mouse group from 2 to 4 weeks after the administration period start (FIG. 3). In FIG. 3, against the diabetes model group with no nepodin administration, * and ** show p<0.05 and p<0.01, respectively.

By this, it was shown that nepodin has the inhibition effect to suppress the elevation of fasting blood glucose level in the diabetes model mice.

Example 4

Effect on glucose tolerance by nepodin administration was measured by using blood glucose level change after the intraperitoneal administration of nepodin to the diabetes model mice.

(1) Methods

Reagents were used as the same as those used in the EXAMPLE 3 as long as there is no special notation.

Intraperitoneal glucose tolerance test (IPGTT) was performed on the sixth week after nepodin administration start. At first, the mice of each group were fasted for 16 hours, and then, glucose was intraperitoneally administered to each mouse at the dose of 2 g/kg.

Blood samples were obtained from the tail vain of each mouse at the time point of 0 min., 30 min., 60 min., 90 min., 120 min., and 180 min. after the glucose administration. Blood glucose level was determined by using Glucose CII Test Wako (Wako Pure Chemical Industries, Ltd.)

(2) Results

Figure 4:
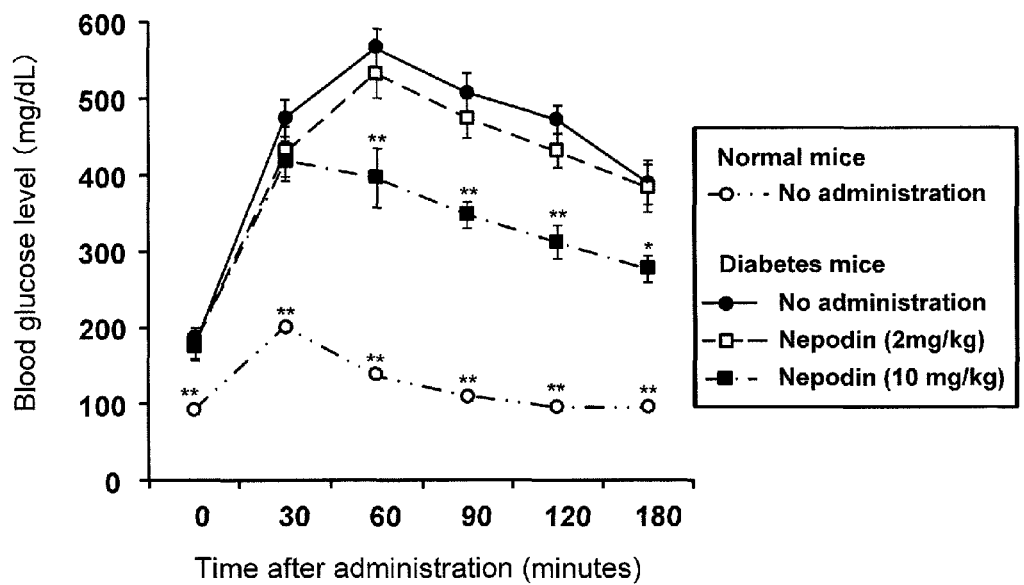
FIG. 4 is the graph showing the time dependent change of the blood glucose level, when the glycemic load (glucose is administrated into intraperitoneal) is given to the diabetes model mouse with nepodin.

The increase of the blood glucose level after glucose load was significantly suppressed in B group (10 mg/kg nepodin was administered) (See FIG. 4). In FIG. 4, against the diabetes model group with no nepodin administration, * and ** show p<0.05 and p<0.01, respectively.

Figure 5:
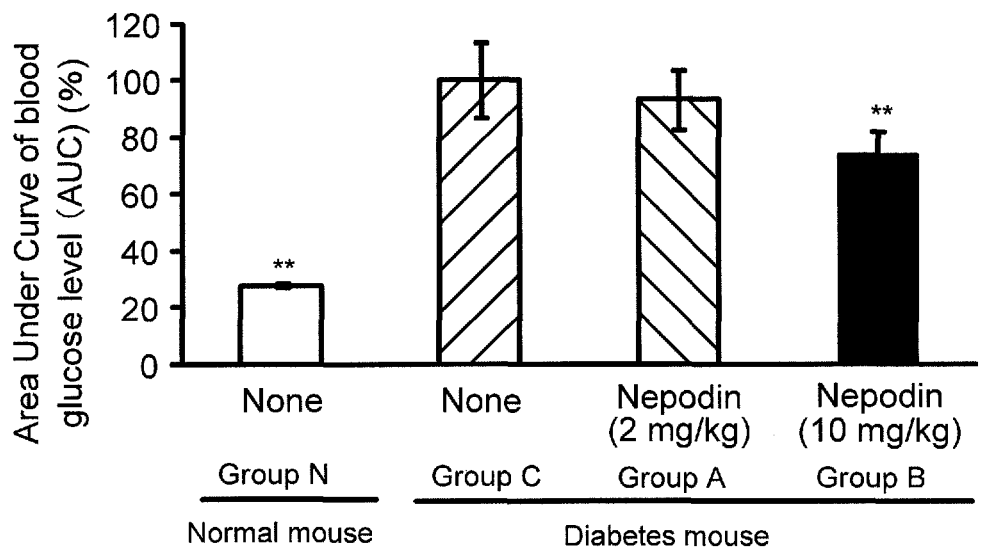
FIG. 5 is the graph showing the area under the curve (AUC) of blood glucose level of each group based on the result shown in FIG. 4.

Also, area under the curve (AUC) of blood glucose levels was shown in FIG. 5, when the AUC of C group (the diabetes mice group with no nepodin administration) was 100%. In FIG. 5, AUC was significantly low in B group. In FIG. 5, against the diabetes model mouse group with no administration, ** shows p<0.01.

As a result, it was demonstrated that nepodin improves the glucose tolerance of the diabetes model mouse.

The results in the above-mentioned examples showed that nepodin suppresses the fasting blood glucose level elevation to improve the glucose tolerance, and that it is effective for the treatment of the diabetes.

Example 5

After the termination of the experiment shown in EXAMPLE 4, the blood samples were obtained from the abdominal aorta of the mice from each group under anesthesia, and they were centrifuged with 1,000×g at room temperature to obtain serum samples. After that, the mice of each group were killed by cervical dislocation to put out of the misery; then organs were excised to use the following experiments.

(1) Effect for Insulin Resistance

Serum insulin level of Lewi's insulin-mouse-T (Shibayagi Co., Ltd.) was determined by ELISA (measurement at the wavelengths of 450 nm and 620 nm), according to protocols written in its package insert.

HOMA-IR (Homeostasis model assessment-Insulin Resistance), which is an index of the insulin resistance, was calculated based on data on both blood glucose and serum insulin, by using following equation.

$$\text{HOMA-IR}=(\text{blood glucose} \times \text{insulin level})/405 \quad (1)$$

HOMA-IR values were obtained from both levels of serum blood glucose and serum insulin of the mice in group N (the normal mice), the administration groups A, B, and C. They were used to investigate for the change of the insulin resistant index. Results are shown in FIG. 6.

Figure 6:
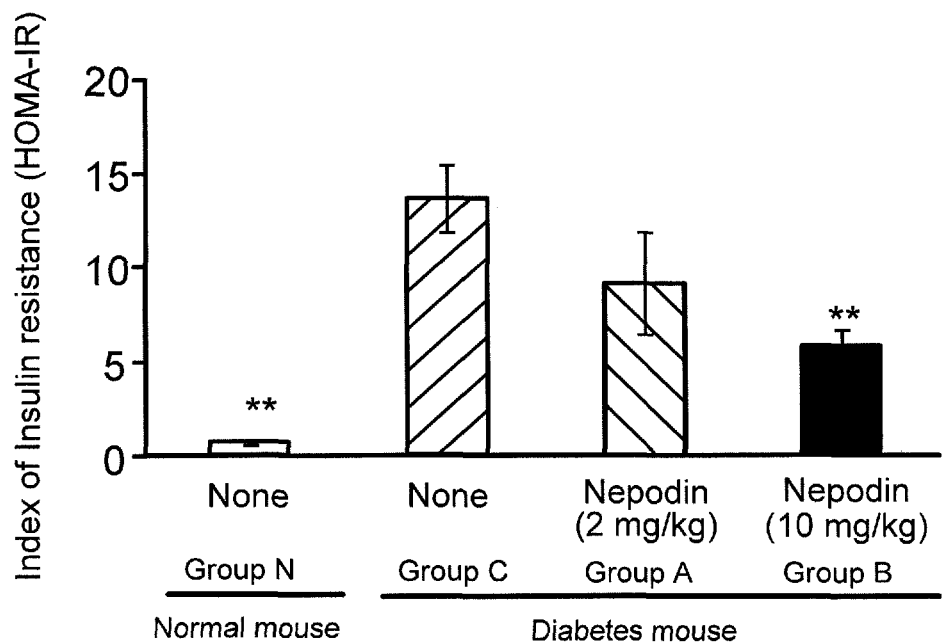
FIG. 6 is the graph showing the homeostasis model assessment ratio (HOMA-IR) of normal and diabetes mouse.

As shown in FIG. 6, in group C (the diabetes model animal, with no nepodin administration), HOMA-IR was high to show that their insulin resistance grow worse. In contrast, in the both groups A and B (nepodin administration group), HOMA-IR was significantly lower (See FIG. 6) (against the no administration diabetes model group, *: $p<0.05$, **: $p<0.01$).

Upon these, it was demonstrated that nepodin has the function to improve the insulin resistant in the diabetes model mice.

(2) Effect on Improvement in Lipid Metabolism

Figure 7A:
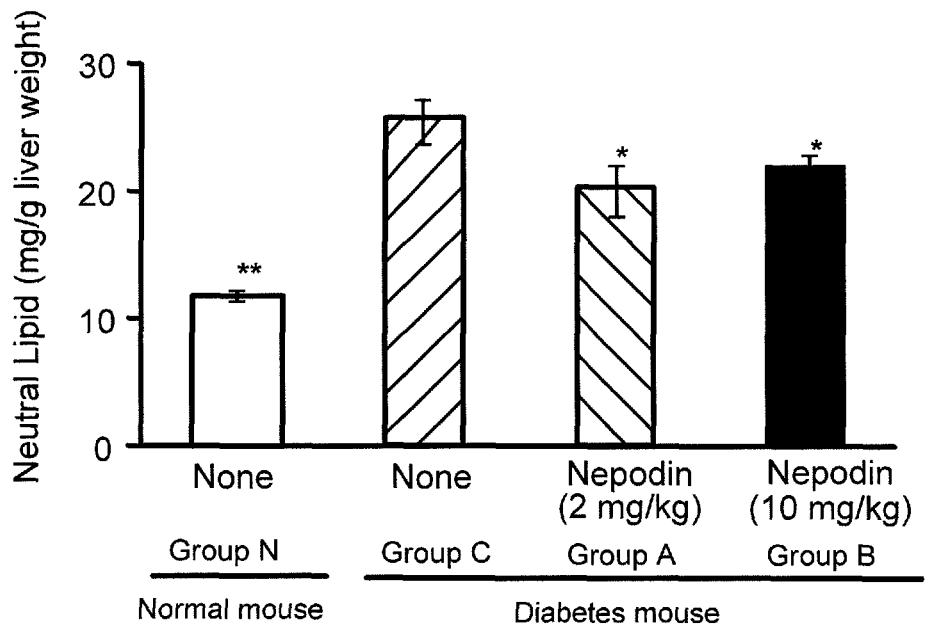
FIG. 7A is the graph showing neutral fat level in liver tissue of the normal and diabetes animal.
Figure 7B:
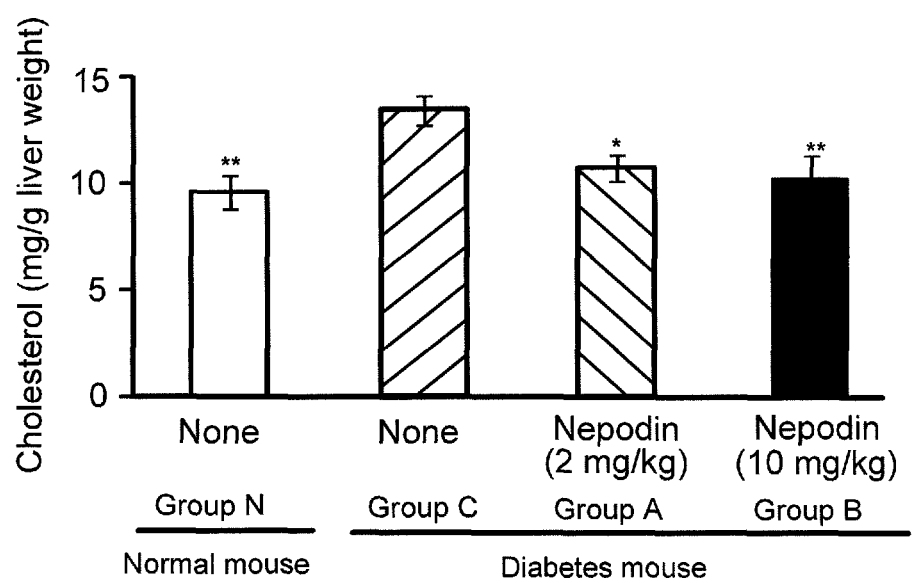
FIG. 7B is a graph showing the cholesterol amount in a mouse liver of normal and diabetes mice.

Livers from the mice of each group were homogenized and total lipid was extracted by using Folch method. Both amounts of neutral lipid and cholesterol in the liver were determined by using LabAssat Tiglyceride (Wako Pure Chemical Industries, Ltd.) and LabAssay Cholesterol (Wako Pure Chemical Industries, Ltd.) Results are shown in FIGS. 7A and 7B.

As compared to the group N (the normal mice), the groups A to C (the diabetes model mice) showed higher neutral lipid level and cholesterol level in the liver. However, the groups A and B (nepodin administration group) showed significantly lower neutral lipid level and cholesterol level in the liver, compared to those of the group C (with no administration) (against the diabetes model group with no administration, *: $p<0.05$, **: $p<0.01$).

The serum neutral lipid (triglyceride) level was determined by using LabAssay Triglyceride (Wako Pure Chemical Industries, Ltd.). The serum cholesterol level was determined by using LabAssay Cholesterol (Wako Pure Chemical Industries, Ltd.). Results are shown in FIGS. 8A and 8B.

Figure 8A:
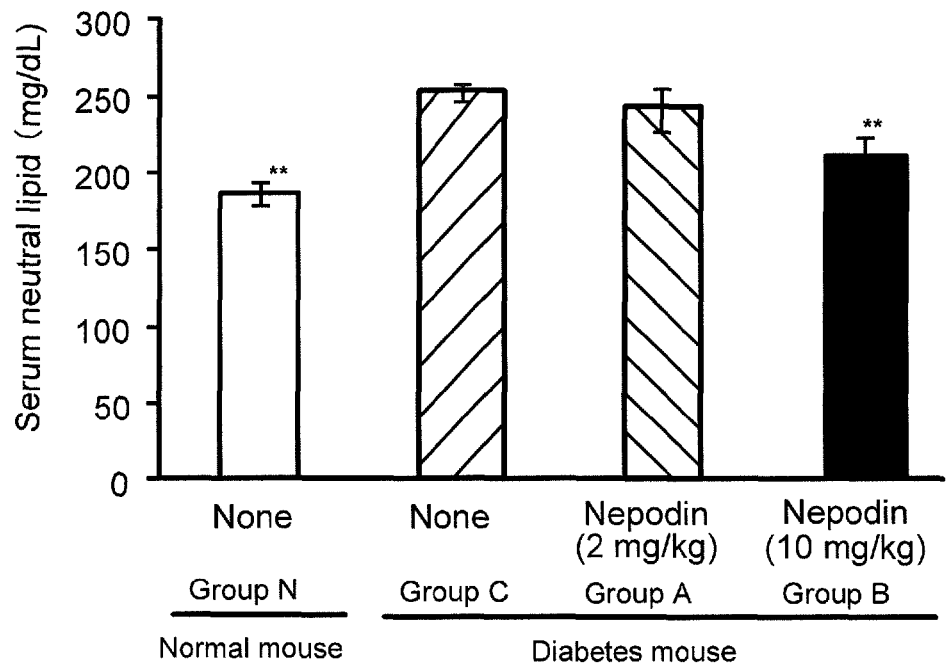
FIG. 8A is a graph showing the triglyceride amount in serum of the normal and diabetes mice.
Figure 8B:
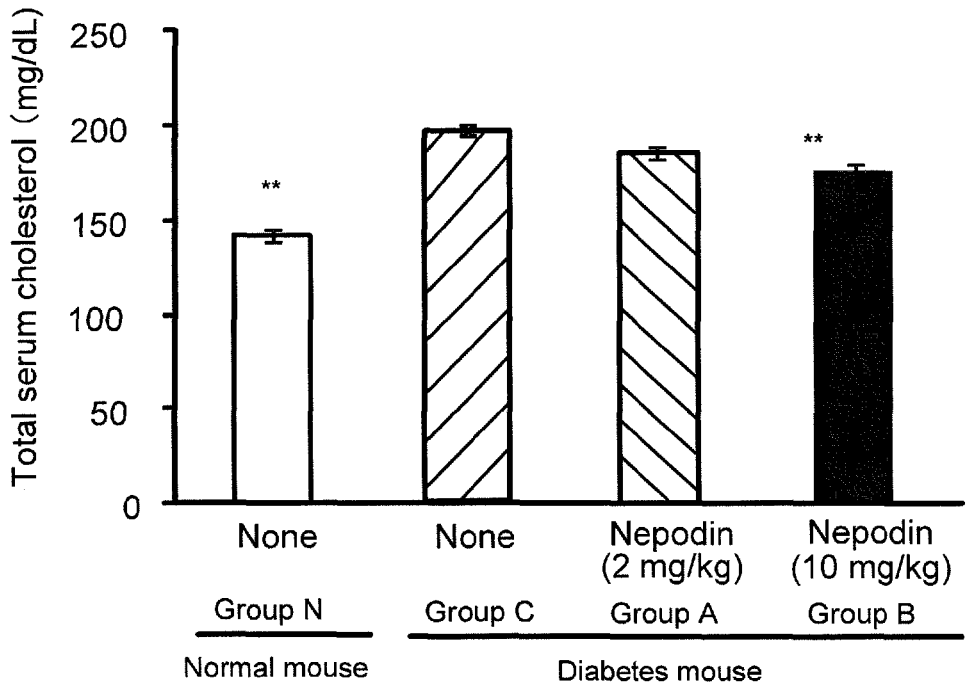
FIG. 8B is a graph showing total cholesterol amount in the serum of the normal and diabetes mice.

As shown in FIGS. 8A and 8B, both levels of the serum neutral lipid and cholesterol in the diabetes model animal were higher compared to those in the normal mice. In contrast, in nepodin administration groups, these levels were significantly lower (against the diabetes model group with no administration, *: $p<0.05$, **: $p<0.01$).

As described above, it was demonstrated that nepodin has the function to improve the lipid metabolism in the diabetes model mice.

(3) Effect on Anti-Oxidizing Action

TBARS value, an index for anti-oxidizing action, was determined by using a TBARS Assay Kit (ZeptoMetrix Co., Inc.).

TBARS values obtained from the mice sera in each group were shown in FIG. 8C. As compared to the group N (the normal mice), the serum TBARS in the group C (the diabetes model mouse) was higher. In contrast, TBARS values in both of the group A and B (nepodin administrated) showed significantly lower (against the diabetes model group with no administration, *: $p<0.05$, **: $p<0.01$).

As a result, it was demonstrated that nepodin has an in vivo anti-oxidizing effect in the diabetes model mice. Since the oxidative stress is an exacerbation factor for diabetes and metabolic syndrome, this shows that nepodin has advantageous effect for the prophylaxis and/or treatment for diabetes or metabolic syndrome.

INDUSTRIAL APPLICABILITY

The invention is useful for medical/pharmaceutical fields.

The invention claimed is:

1. A method for activating an adenosine monophosphate-activated protein kinase (AMPK), comprising: administering to a patient an AMPK activating agent, wherein the AMPK activating agent comprises at least one selected from the group consisting of a compound shown in the following chemical formula (I), a pharmacologically acceptable salt thereof, and a pharmacologically acceptable hydrates thereof as an active ingredient

[Chemical formula 1]

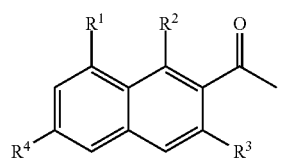

(I)

(In the formula, $R_1$ to $R_4$ independently show one of substitute selected from the group consisting of a hydrogen atom, hydroxyl group, alkyl group having a carbon number 1 to 3, alkoxy group having the carbon number 1 to 3, and acyl group having the carbon number 1 to 3 respectively.)

2. The method according to the claim 1, wherein in the chemical formula (I), $R_1$ and $R_2$ are a functional group selected from the group consisting of hydroxyl group, methoxy group, ethoxy group, and acetyl group respectively, $R_3$ and $R_4$ are a functional group a hydrogen atom, methyl group, and ethyl group respectively.

3. The method according to the claim 1, wherein the AMPK activating agent comprises at least one selected from the group consisting of a compound shown in the following chemical formula (II), a pharmacologically acceptable salt thereof, and a pharmacologically acceptable hydrates thereof as an active ingredient

[Chemical formula 2]

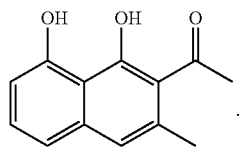

(II)

4. The method according to the claim 1, wherein the patient is in need of prevention and/or treatment of metabolic syndrome.

5. The method according to the claim 1, wherein the patient is in need of acceleration of glucose uptake.

6. The method according to the claim 1, wherein the patient is in need of improvement of glucose tolerance.

7. The method according to the claim 1, wherein the patient in need of reduction of blood lipid level.

8. The method according to the claim 1, wherein the patient is in need of amelioration of glucose metabolism and lipid metabolism.

* * * * *